(12) United States Patent
Green et al.

(10) Patent No.: US 9,857,334 B2
(45) Date of Patent: Jan. 2, 2018

(54) ION MOBILITY SEPARATION BUFFER GAS COMPOSITION

(71) Applicant: Micromass UK Limited, Wilmslow (GB)

(72) Inventors: Martin Raymond Green, Bowdon (GB); Keith George Richardson, High Peak (GB)

(73) Assignee: MICROMASS UK LIMITED, Stamford (GB)

(*) Notice: Subject to any disclaimer, the term of this patent is extended or adjusted under 35 U.S.C. 154(b) by 0 days.

(21) Appl. No.: 15/098,780

(22) Filed: Apr. 14, 2016

(65) Prior Publication Data

US 2016/0305907 A1    Oct. 20, 2016

(30) Foreign Application Priority Data

Apr. 14, 2015  (GB) .................................. 1506302.7

(51) Int. Cl.
  *H01J 49/00* (2006.01)
  *H01J 49/04* (2006.01)
  *H01J 49/26* (2006.01)
  *G01N 27/62* (2006.01)

(52) U.S. Cl.
  CPC .......... *G01N 27/622* (2013.01); *H01J 49/004* (2013.01)

(58) Field of Classification Search
  CPC .... G01N 27/622; G01N 27/624; C07B 63/00; H01J 49/0031; H01J 49/004; H01J 49/0027; H01J 49/0077
  USPC ........ 250/281, 282, 287, 288, 283, 284, 379
  See application file for complete search history.

(56) References Cited

U.S. PATENT DOCUMENTS

| | | | | |
|---|---|---|---|---|
| 4,777,363 A | * | 10/1988 | Eiceman | G01N 27/622 250/286 |
| 6,765,198 B2 | * | 7/2004 | Jenkins | G01N 27/622 250/282 |
| 7,015,462 B2 | * | 3/2006 | Karas | G01N 27/622 250/282 |
| 7,015,464 B2 | * | 3/2006 | Nagano | H01J 49/0027 250/282 |
| 7,026,612 B2 | * | 4/2006 | Guevremont | H01J 49/04 250/281 |
| 7,119,328 B2 | * | 10/2006 | Kaufman | G01N 27/624 250/281 |
| 7,129,482 B2 | * | 10/2006 | Miller | G01N 27/624 250/281 |
| 7,388,197 B2 | | 6/2008 | McLean et al. | |
| 7,608,818 B2 | | 10/2009 | Miller et al. | |
| 7,820,962 B2 | * | 10/2010 | Wynn | G01N 27/622 250/281 |

(Continued)

OTHER PUBLICATIONS

Ziegler et al., "Weak Ion-Molecule Interactions in the Gas Phase: A High-Pressure Mass Spectrometry and Computational Study of Chloride-Alkane Interactions", J. Phys. Chem., vol. 117, pp. 5785-5793, 2013.

(Continued)

*Primary Examiner* — David A Vanore (57) ABSTRACT

A method of separating ions comprises causing ions to separate according to their ion mobility or differential ion mobility by virtue of their interactions with a buffer gas within an ion mobility or differential ion mobility separation device. The buffer gas comprises one or more organic, organosilicon or silicon-based compounds.

13 Claims, 1 Drawing Sheet

(56) References Cited

U.S. PATENT DOCUMENTS

| | | | | |
|---|---|---|---|---|
| 7,956,323 | B2* | 6/2011 | Morley | G01N 27/622 |
| | | | | 250/281 |
| 7,964,028 | B2* | 6/2011 | Harvey | B01J 20/26 |
| | | | | 73/31.01 |
| 8,334,502 | B2 | 12/2012 | Giles | |
| 8,384,024 | B2* | 2/2013 | Miller | G01N 27/624 |
| | | | | 250/281 |
| 8,552,366 | B2 | 10/2013 | Hoyes | |
| 8,581,178 | B2* | 11/2013 | Miller | G01N 27/624 |
| | | | | 250/282 |
| 8,640,727 | B2* | 2/2014 | Zhang | G01N 27/622 |
| | | | | 137/205.5 |
| 9,134,273 | B2* | 9/2015 | LeBlanc | H01J 49/00 |
| 9,257,269 | B2* | 2/2016 | Wu | C07B 63/00 |
| 9,406,492 | B1* | 8/2016 | Ramsey | B01L 3/5027 |
| 9,425,031 | B2* | 8/2016 | Schneider | G01N 27/624 |
| 2008/0173809 | A1* | 7/2008 | Wu | C07B 63/00 |
| | | | | 250/283 |
| 2009/0179145 | A1* | 7/2009 | Crouch | G01N 27/622 |
| | | | | 250/281 |
| 2009/0224147 | A1* | 9/2009 | Mie | C07B 63/00 |
| | | | | 250/282 |
| 2011/0114210 | A1* | 5/2011 | Zhang | G01N 27/622 |
| | | | | 137/602 |
| 2016/0187296 | A1* | 6/2016 | Blagojevic | G01N 27/624 |
| | | | | 250/282 |

OTHER PUBLICATIONS

Bradley B. Schneider et al., "DMS-MS Separations with Different Transport Gas Modifiers", International Journal for Ion Mobility Spectrometry, vol. 16, No. 3, pp. 207-216, Mar. 2013.

Sven Roetering et al., "Effect of Dopants on the Analysis of Pesticides by Means of Differential Mobility Spectrometry with Atmospheric Pressure Photoionization", International Journal for Ion Mobility Spectrometry, vol. 13, No. 2, pp. 47-54, Jul. 2010.

Andriy Kuklya et al., "Non-Polar Modifier Assisted Analysis of Aromatic Compounds by Means of Planar Differential Ion Mobility Spectrometry with a 63 Ni Ionization Source", Analytical Methods, vol. 7, No. 5, pp. 2101-2106, Jan. 2015.

* cited by examiner

ION MOBILITY SEPARATION BUFFER GAS COMPOSITION

CROSS-REFERENCE TO RELATED APPLICATION

This application claims priority from and the benefit of United Kingdom patent application No. 1506302.7 filed on 14 Apr. 2015. The entire contents of this application are incorporated herein by reference.

FIELD OF THE INVENTION

The present invention relates generally to mass spectrometry and in particular to devices for and methods of separating ions according to their ion mobility or differential ion mobility. The invention also extends to a mass spectrometer and method of mass spectrometry including such a device.

BACKGROUND

The basic principles of ion mobility separation ("IMS") and ion mobility separation devices are well established—generally, ions are urged through a gas-filled region using an electric field and caused to separate by virtue of their differential interactions with molecules of the background or "buffer" gas. The nature and number of these interactions experienced by a particular species of ion will depend on the shape and/or size of the ion and may be described by the ion's effective collision cross section. Known techniques for ion mobility separation include drift tube ion mobility separation, where ions are caused to separate along a constant axial field gradient and travelling wave ion mobility separation, wherein ions are caused to separate by one or more transient DC (or AC) waves.

It is also known to separate or filter ions according to the dependence of their ion mobility on field strength e.g. using an asymmetric periodic DC field. This may be referred to as differential mobility spectrometry ("DMS") or field assisted ion mobility separation ("FAIMS").

Ion mobility separation may be used by itself to analyse samples, in which case an ion detector will be disposed at the end of an ion mobility separation device. Alternatively, ion mobility separation may be combined with downstream mass analysis to provide two degrees of separation and e.g. a higher resolution.

It is desired to provide improved methods and devices for use in such ion mobility separation instruments and applications.

SUMMARY

According to an aspect there is provided a method of separating ions comprising:
providing an ion mobility or differential ion mobility separation device; and
causing ions to separate within the device according to ion mobility or differential ion mobility by virtue of their interactions with a buffer gas, wherein the buffer gas comprises one or more organic, organosilicon or silicon-based compounds containing two or more carbon or silicon atoms.

The various embodiments provide improvements in ion mobility separation selectivity. This is achieved by introducing one or more organic, organosilicon or silicon-based compounds as the ion mobility separation buffer gas. These compounds have been found to possess a combination of physical and chemical characteristics that are particularly advantageous. For instance, they are generally amongst the most polarisable compounds relative to their molecular weight and/or radius and hence give rise to relatively large charge-induced dipole interactions with analyte ions when introduced into an ion mobility separation device as a buffer gas. This is particularly true for hydrocarbon, hydrosilane and hydrosilicon compounds which may be used according to various embodiments.

The interactions between the analyte ions and the buffer gas determine the separation characteristics of the ion mobility separation device and selecting a suitable gas composition that optimises or enhances these interactions provides an increased ion mobility separation specificity and/or peak capacity. By using highly polarisable compounds as the buffer gas, a further degree of ion mobility separation selectivity based e.g. on the electronic charge distribution of the ions is provided.

Furthermore, the various buffer gas compounds described herein may generally have relatively low (or zero) permanent dipole moments such that they tend to be gaseous or volatile at room temperatures (20° C.). More polar molecules i.e. those having larger permanent dipole moments and having a similar molecular weight and/or polarisabiltiy typically have higher boiling points and may exist only in the liquid state at room temperature (20° C.). By contrast to these more polar molecules, the compounds according to various embodiments can be introduced into an ion mobility separation device relatively easily in the gaseous state, and in a controlled manner, without requiring an elaborate or expensive heated buffer gas interface.

Additionally, the hydrocarbon, hydrosilicon or hydrosilane compounds according to various embodiments tend be inert and non-corrosive so their use does not introduce any additional problems in this respect.

It will be understood that organic compounds, by definition, contain carbon. Organic compounds typically also contain hydrogen (i.e. or deuterium) atoms, although some organic compounds, e.g. fluorocarbons, may not. Conventionally, and for the purposes of the present application, the term "organic" does not include simple carbon oxides such as CO or $CO_2$ etc. Organosilicon compounds are analogous compounds where one or more carbon atom is replaced by a silicon atom i.e. they contain carbon and silicon atoms. Silicon-based compounds are generally similar but contain silicon instead of carbon.

The phrase "containing two or more carbon or silicon atoms" is intended to be understood to mean that the compound(s) may contain any suitable combination of carbon and silicon atoms provided that there are at least two e.g. two or more carbon atoms, two or more silicon atoms, or one or more carbon atom and one or more silicon atom.

The one or more organic, organosilicon or silicon-based compounds may comprise one or more hydrocarbon, hydrosilicon or hydrosilane compounds.

It is noted that any reference herein or feature described in relation to one or more organic, organosilicon or silicon-based compounds thus also applies specifically, in various embodiments, to hydrocarbons, hydrosilicons or hydrosilanes.

It will be understood that the term hydrocarbon is intended to refer to compounds consisting of carbon-carbon and carbon-hydrogen bonds. Similarly, a hydrosilicon compound is one that consists of silicon-silicon and silicon-hydrogen bonds. The term hydrosilane refers to compounds containing a mixture of bonds selected from the group consisting of carbon-carbon, carbon-silicon, carbon-hydrogen and silicon-hydrogen bonds. For example, a hydrosilane may be a hydrocarbon where one or more carbon atoms are replaced by silicon atoms, or alternatively a hydrosilicon compound with one or more of the silicon atoms replaced by a carbon atom or alkyl group. It will be appreciated that the compounds used herein may generally be branched or unbranched, and may contain any suitable arrangement of carbon-carbon, carbon-silicon or silicon-silicon single, double or triple bonds.

The one or more organic, organosilicon or silicon-based compounds constituting the buffer gas may in embodiments be selected from the group of hydrocarbon, hydrosilicon or hydrosilane compounds excluding methane ($CH_4$) and/or silane ($SiH_4$). Generally, the larger the compound the more polarisable it will be. Larger compounds may also provide additional specificity based on charge-induced structural distortions, changes in conformation or rearrangements.

In various embodiments, the buffer gas may comprise one or more organic, organosilicon or silicon-based compounds, and optionally one or more hydrocarbon, hydrosilicon or hydrosilane compounds, containing three or more, four or more, five or more or six or more carbon or silicon atoms. It has been identified that organic, organosilicon or silicon-based compounds containing five or more carbon or silicon atoms are particularly advantageous since they are generally larger and more polarisable and may also provide additional specificity based on greater charge-induced structural distortions, changes in conformation or rearrangements.

It is also contemplated, for instance, that the buffer gas may comprise one or more halogenated organic, organosilicon or silicon-based compounds. For example, the organic, organosilicon or silicon-based compounds described herein may comprise one or more fluorocarbon or hydrofluorocarbon compounds.

Other embodiments also extend to the use of deuterated compounds, for instance deuterated hydrocarbons, deuterated hydrosilicons or deuterated hydrosilanes. For the purposes of the present application it will be understood, therefore, that the prefix "hydro-" as used herein also includes analogous compounds where one or more (or all of the) hydrogen atoms are replaced with deuterium atoms. That is, any reference to hydrocarbons, hydrosilicons or hydrosilanes used herein is also intended to cover deuterated hydrocarbons, deuterated hydrosilicons or deuterated hydrosilanes.

The one or more organic, organosilicon or silicon-based compounds may comprise substantially 100% by volume of the total buffer gas composition. By substantially 100%, it is meant that any trace compounds or contaminants having no significant interaction with the analyte ions may be ignored i.e. that the buffer gas may consist of or consist essentially of the one or more organic, organosilicon or silicon-based compounds. These embodiments are particularly advantageous in that they allow the one or more organic, organosilicon or silicon-based compounds to have a greater influence on the ions within the device. The buffer gas may comprise a mixture containing one or more organic, organosilicon or silicon-based simultaneously introduced into the ion mobility separation device.

Alternatively, the one or more organic, organosilicon or silicon-based compounds may comprise less than 100% by volume of the total buffer gas composition. For instance, the one or more organic, organosilicon or silicon-based compounds may comprise: (i) about 90%; (ii) about 80%; (iii) about 70%; (iv) about 60%; (v) about 50%; (vi) about 40%; (vii) about 30%; (viii) about 20%; (ix) about 10%; or (x) less than about 10% by volume of the total buffer gas composition. Again, embodiments in which the one or more organic, organosilicon or silicon-based compounds comprise a relatively higher proportion by volume of the total buffer gas composition are particularly advantageous in that they allow those compounds to have a greater influence on the ions within the device. In these cases, the buffer gas may be a mixture comprising the one or more organic, organosilicon or silicon-based compounds and may also contain any other suitable gas(es) e.g. conventional ion mobility separation buffer gases such as argon, nitrogen or helium.

The ion mobility or differential ion mobility separation device may comprise any known or conventional ion mobility or differential ion mobility separation device. For instance, and particularly, the device may comprise a drift tube ion mobility separation device or a travelling wave ion mobility separation device. The device may comprise a plurality of electrodes. The plurality of electrodes may define an ion guiding or transmission region along which ions are caused to separate. The ion mobility or differential ion mobility separation device may accordingly include means arranged to apply one or more electric fields across the ion guiding or transmission region and/or to the plurality of electrodes, and the method may generally further comprise a step of applying one or more electric fields to the device to urge ions through the device and/or to cause ions to separate within the device. The applied electric field(s) may comprise any suitable combination of static or transient and AC or DC fields. For instance, where the device is a drift tube device, the applied electric field may comprise an axial DC gradient i.e. a linear DC field along the axis of ion transmission. Where the device is a travelling wave device, the applied field may comprise one or more transient AC or DC waves. Where the device is a differential ion mobility device the electric field may comprise a periodic asymmetric waveform and, optionally, an axial DC gradient.

The ions that are caused to separate within the ion mobility or differential ion mobility separation device may be generated at an ion source disposed upstream of the device. The method may generally, therefore, involve generating analyte ions at or with an ion source and passing the analyte ions to the ion mobility or differential ion mobility separation device. The ion source may comprise any known ion source. The analyte ions may be passed directly to the device from the ion source, or may be passed through any suitable ion optical arrangement prior to being passed to the device. The analyte ions may be passed to the device after one or more stages of separation, e.g. after liquid chromatographic ("LC") or gas chromatographic ("GC") pre-separation, and/or after one or more stages of ion trapping. It will be understood that various embodiments are not particularly limited in this respect. The analyte ions may be passed through the device multiple times, i.e. in multiple directions. For instance, analyte ions may be generated upstream, passed through the device in a first direction, fragmented downstream and then passed back through the device in the opposite direction.

Generally, the buffer gas is introduced, in use, to the device via an interface. This interface may be separate from the apertures through which analyte ions enter/exit the device, although it need not be. The method may generally therefore comprise a step of introducing a buffer gas to the ion mobility or differential ion mobility separation device through such interface. It will be appreciated that the step of generating the analyte ions is distinct from the step of introducing the buffer gas i.e. the analyte ions do not derive from the buffer gas.

The ions may be confined within the device in at least one radial direction by one or more RF or AC potentials.

Alternatively/additionally, the ions may be radially focussed at the exit of the ion mobility separation device. Ions may be focussed using any suitable ion optic arrangement, e.g. using one or more lenses or ion funnels.

The one or more organic, organosilicon or silicon-based compounds may comprise volatile or gaseous at room temperature (20° C.) and atmospheric pressure (1013 mbar).

The buffer gas may comprise one or more organic, organosilicon or silicon-based compounds having a boiling point of less than about: (i) 35° C.; (ii) 30° C.; (iii) 25° C.; (iv) 20° C.; or (v) 15° C. at atmospheric pressure (1013 mbar).

This is advantageous because it is significantly simpler to controllably introduce gas into an ion mobility separation device (e.g. compared to liquid dopants). For example, when the compounds are gaseous or volatile a need for any significant heating of the buffer gas interface or the device is avoided. The compounds may be introduced directly in gaseous form or may be volatised e.g. by a pressure drop across the interface e.g. where the device is operated at sub-atmospheric pressure.

It is also contemplated at least in some embodiments that compounds with higher boiling points that remain liquid at room temperature (20° C.) may be used. In this case, it may be necessary to e.g. decrease the operating and/or interface pressure or increase the operating and/or interface temperature to provide the buffer gas. Although this may require a more elaborate buffer gas interface, the number and type of compounds that can be introduced as buffer gas may be extended such that, for instance, compounds having even higher molecular weights and/or polarisabilities (e.g. higher molecular weight hydrocarbons) can be used.

The one or more organic, organosilicon or silicon-based compounds may be aliphatic.

Aliphatic compounds tend to have lower boiling points than aromatic compounds of similar size or similar numbers of carbon atoms and are thus generally better suited for use or introduction as an ion mobility separation buffer gas. The buffer gas may comprise one or more aliphatic hydrocarbon, aliphatic hydrosilicon or aliphatic hydrosilane compounds.

Aromatic compounds may, however, also be highly polarisable and so in principle may also be used in embodiments e.g. provided that they have a suitably low boiling point and/or the buffer gas interface is heated. The skilled person will be able to identify suitable aromatic compounds having the desired characteristics for a given application.

The buffer gas may comprise one or more alkanes containing two or more carbon atoms and that are gaseous at room temperature (20° C.) and atmospheric pressure (1013 mbar).

In particular, the buffer gas may comprise or consist of ethane, propane, butane, isobutene, cyclopropane, cyclobutane and/or neopentane, or may comprise a mixture containing any of these compounds.

The method may comprise selecting or altering the composition of the buffer gas to enhance the separation characteristics of the ion mobility or differential ion mobility separation device by controlling or altering the interactions between at least some of the ions and the buffer gas.

The method may comprise selecting or adjusting the buffer gas composition to enhance or change the separation characteristics of the ion mobility or differential ion mobility separation device for a known analyte ion.

The method may comprise enhancing the separation characteristics of the device by selectively altering the interactions between at least some of the ions and the buffer gas. The separation characteristics of the device include e.g. its specificity and/or resolution, and are defined by virtue of the differences in apparent interaction cross section for different analyte ions. By enhancing or altering the apparent interaction cross sections for some or all of the analyte ions passing through the device, the extent to which these ions are separated from each other by the device is altered, and optionally increased. The separation characteristics of the device may be increased broadly e.g. for substantially all analyte ions, by enhancing or increasing the magnitude of the interactions. Naturally, it is also possible to tailor the buffer gas composition to selectively enhance an interaction of a specific analyte ion of interest, e.g. to provide better separation of this ion from otherwise similar species.

The buffer gas may consist of the one or more organic, organosilicon or silicon-based compounds. The buffer gas may comprise or consist of a mixture of the one or more organic, organosilicon or silicon-based compounds. The mixture may also contain one or more other compounds, such as one or more compounds conventionally used as ion mobility separation buffer gas e.g. argon or nitrogen gas. The one or more compounds may be introduced simultaneously into the device. The relative composition of the one or more compounds may be adjusted to alter the composition of the buffer gas. This may be achieved by providing a gas manifold connected to a plurality of supplies of gas. The buffer gas composition may be adjusted dynamically or in real-time during the course of an experiment. The buffer gas composition may be adjusted or controlled in a pre-determined manner, e.g. based on previous or calibration experiments. The buffer gas composition may be selected based on knowledge of a known target analyte ion to increase the specificity of the separation.

The method may comprise operating the ion mobility or differential on mobility device at sub-atmospheric pressure.

The device may be operated at pressures less than: (i) about 1000 mbar; (ii) about 100 mbar; (iii) about 10 mbar; (iv) about 1 mbar; or (v) about 0.1 mbar. Operating the device at sub-atmospheric pressure may facilitate the volatilisation of volatile compounds and/or ensure that the compounds remain in the gaseous state in use.

The buffer gas may comprise one or more chiral compounds.

A number of organic, organosilicon, and silicon-based compounds are chiral. When such compounds are used as ion mobility separation buffer gas this may provide additional specificity for separating chiral analyte ions.

The analyte ions may comprise or be derived from: (i) peptides; (ii) lipids; (iii) metabolites; (iv) carbohydrates; (v) drugs; (vi) pesticides; (vii) a biological sample; or (viii) a pharmaceutical sample.

The analyte ions may generally be derived from any sample of interest. It will be appreciated that the buffer gas compositions described herein are suitable for general purpose ion mobility separation devices and are not limited to specific applications or experiments.

The method may further comprise analysing the or at least a portion of the ions according to mass or mass to charge ratio and generating combined ion mobility and mass spectral data.

The step of analysing ions according to mass or mass to charge ratio may follow the step of separating ions according to (differential) ion mobility i.e. a mass analyser may be provided downstream of the ion mobility separation device. The method may further comprise transmitting, filtering and/or reacting or fragmenting ions prior to the mass analysis.

The combined ion mobility and mass spectral data may be a two dimensional spectra. Because the timescales for ion mobility separation are typically much longer than those for mass or mass to charge ratio separation, the mass or mass to charge ratio analysis may be nested i.e. multiple mass or mass to charge ratio analyses may be performed within the course of a single ion mobility separation.

According to another aspect there is provided a device for separating ions according to their ion mobility or differential ion mobility by virtue of their interactions with a buffer gas, wherein the buffer gas comprises one or more organic, organosilicon or silicon-based compounds containing two or more carbon or silicon atoms.

The device may be any known ion mobility separation or differential mobility separation ("DMS") device e.g. the device may be a device as described above in relation to the various aspects discussed above. In particular, as discussed above, the device may generally comprise means for applying one or more electric fields to the device. The one or more applied electric fields may comprise any suitable DC or AC and static or transient electric fields depending on the nature of the device. For instance, the one or more applied electric fields may comprise a linear axial DC gradient. Alternatively/additionally, the one or more applied electric fields may comprise one or more transient DC electric fields or potential wells. The one or more applied electric fields may also comprise a periodic asymmetric waveform, e.g. where the device separates ions according to differential ion mobility. The one or more applied electric fields may act, in use, to urge at least some of the ions through the device. The ions will generally separate during their passage through the device e.g. along the axis of the device between an ion entrance and ion exit of the device.

The buffer gas in this aspect may be a buffer gas or comprise any or all of the features of the buffer gas as described above in relation to the various aspects discussed above.

The device may comprise a gas controller arranged and adapted to adjust the composition of the buffer gas introduced to the device so as to selectively change or enhance the separation characteristics of the device.

From another aspect there is provided a mass spectrometer comprising a device substantially as described or containing any or all of the features described above and a mass analyser.

The mass analyser may comprise: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; or (xiv) a linear acceleration Time of Flight mass analyser.

The mass spectrometer may comprise various additional known components e.g. ion optics, ion fragmentation or reaction devices, ion filters or analysers arranged in any suitable configuration. For instance, the mass spectrometer may comprise, sequentially, an ion source (e.g. an electrospray ionisation source), an ion trap or trapping funnel, a device for separating ions according to ion mobility or differential ion mobility as described herein, ion focussing and/or filtering optics and a mass analyser (e.g. an orthogonal Time of Flight mass analyser).

The mass spectrometer may alternatively comprise, sequentially, a device for separating ions according to ion mobility or differential ion mobility as described herein, an ion trap or trapping region for collecting ions and subsequently injecting ions into a mass analyser and a mass analyser (e.g. an ion trap or an electrostatic mass analyser arranged to generate an electrostatic field having a quadro-logarithmic potential distribution). Where the ion mobility separation or differential ion mobility separation device is provided at the front of the instrument it may be provided or sold as a separate component arranged to interface or mount to the mass spectrometer.

According to another aspect there is provided a method of separating ions according to their ion mobility or differential ion mobility comprising:

providing an ion mobility or differential ion mobility separation device; and causing ions to separate according to ion mobility or differential ion mobility by virtue of their interactions with a buffer gas within the device, wherein the buffer gas comprises one or more organic, organosilicon or silicon-based compounds.

According to another aspect there is provided a device for separating ions according to their ion mobility or differential ion mobility by virtue of their interactions with a buffer gas, wherein the buffer gas comprises one or more organic, organosilicon or silicon-based compounds.

The buffer gas in these (and in any of the above) aspects may comprise one or more organic, organosilicon or silicon-based compounds other than methane or carbon dioxide. For the purposes of the present application, it will be understood that the term organic excludes carbon dioxide. Naturally, where the buffer gas is a mixture containing one or more organic, organosilicon or silicon-based compounds other than methane (or carbon dioxide), then the buffer gas may also contain methane or carbon dioxide additional to the one or more one or more organic, organosilicon or silicon-based compounds.

The buffer gas may comprise one or more hydrocarbon, fluorocarbon, hydrofluorocarbon, hydrosilicon or hydrosilane compounds. These compounds may be aliphatic.

The buffer gas may comprise a buffer gas as described above or comprising any of the features described above in relation to the previous aspects to the extent they are not mutually incompatible. Particularly, the organic, organosilicon or silicon-based compounds constituting the buffer gas may be volatile or gaseous at room temperature (20° C.) and atmospheric pressure (1013 mbar). More particularly, the organic, organosilicon or silicon-based compounds may contain two or more carbon or silicon atoms.

These further aspects are compatible with and may be combined with any or all of the features described above in relation to any of the earlier aspects to the extent that they are not mutually incompatible.

In any of the aspects or embodiments described herein, one or more of the organic, organosilicon or silicon-based compounds constituting the buffer gas may have a polarisability greater than about: (i) $2\times10^{-24}$ cm$^3$; (ii) $3\times10^{-24}$ cm$^3$; (iii) $4\times10^{-24}$ cm$^3$; (iv) $5\times10^{-24}$ cm$^3$; (v) $6\times10^{-24}$ cm$^3$; (vi) $7\times10^{-24}$ cm$^3$; (vii) $8\times10^{-24}$ cm$^3$; (viii) $9\times10^{-24}$ cm$^3$; (ix) $10\times10^{-24}$ cm$^3$; and (x) $15\times10^{-24}$ cm$^3$.

In any of the aspects or embodiments described herein, one or more of the organic, organosilicon or silicon-based compounds constituting the buffer gas may have a molecular weight greater than about: (i) 15; (ii) 25; (iii) 35; (iv) 45; (v) 55; (vi) 65; (vii) 75; (viii) 85; (ix) 95; and (x) 100.

In any of the aspects or embodiments described herein, one or more of the organic, organosilicon or silicon-based compounds constituting the buffer gas may have a permanent dipole moment less than about: (i) 1 Debye; (ii) 0.8 Debye; (iii) 0.6 Debye; (iv) 0.4 Debye; (v) 0.2 Debye; (vi) 0.1 Debye; or (vii) a permanent dipole moment of substantially 0 Debye. One or more of the organic, organosilicon or silicon-based compounds may be symmetric.

In any of the aspects or embodiments described herein, one or more of the organic, organosilicon or silicon-based compounds constituting the buffer gas may be selected from the lists of compounds in Table 1 or Table 2 below other than methane.

According to another aspect there is provided a method of improving ion mobility separation selectivity comprising:

(i) providing an ion mobility separation device; and (ii) introducing gaseous hydrocarbon molecules into an ion mobility separation device such that the drift time of analyte ions are selectively altered due to interaction between the analyte ions and the hydrocarbon molecules during their passage through the device.

The gaseous hydrocarbon may have a boiling point of less than or equal to 30° C. at atmospheric pressure.

The hydrocarbon may be chosen from the lists of compounds described below.

The hydrocarbon may comprise 100% or <100% of the ion mobility separation buffer gas.

More than one hydrocarbon species may be introduced simultaneously.

The ion mobility separation device may be operated at sub ambient pressure

The ion mobility separation device may use RF confinement.

The hydrocarbons may contain two or more carbon atoms.

The features of the devices or methods described in relation to any of the aspects or embodiments described above are compatible with and may be combined with each other to the extent that they are not mutually exclusive. In particular, any of the features described in relation to any one of the aspects above may also be applied to any or all of the other aspects to the extent that they are not incompatible.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; (xxviii) a Laser Ablation Electrospray Ionisation ("LAESI") ion source; and (xxix) a Surface Assisted Laser Desorption Ionisation ("SALDI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the device further comprises means arranged and adapted to supply an AC or RF voltage to the electrodes of the device. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage optionally has a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector optionally selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD").

Additionally or alternatively, the chromatography detector may comprise a non-destructive chromatography detector optionally selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide is optionally maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions are optionally caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions optionally comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

BRIEF DESCRIPTION OF THE DRAWING

Various embodiments will now be described, by way of example only, and with reference to the accompanying drawing in which.

DETAILED DESCRIPTION

In ion mobility separation (or differential mobility separation ("DMS")) experiments generally, analyte ions are urged through a gas-filled device by some combination of static and/or transient AC and/or DC electric fields and caused to separate according to their interactions with the background gas. This gas is referred to as the buffer gas, or alternatively as the "drift" gas. The nature and magnitude of the interactions between different ions and the buffer gas may be described by the apparent interaction cross sections of the analyte ions. The cross section of an analyte ion depends on its size and shape i.e. stereochemistry. Ions having a low interaction cross section will undergo relatively few interactions and may pass through the buffer gas relatively quickly or easily. The separation characteristics of the ion mobility separation device are defined by the extent to which different ions can be separated from each other in the device.

It has been recognised that where the buffer gas contains polarisable molecules, the interactions between analyte ions and the buffer gas (and hence the apparent interaction cross section of the analyte ions) are also affected by the electronic charge distributions of the analyte ion and the buffer gas molecules. In particular, it has been found that introducing polarisable buffer gases into an ion mobility separation device results in selective charge-induced dipole interactions between the ions and the buffer gas molecules. These interactions thus alter the separation characteristics of the device. The magnitude of these charge-induced dipole interactions, and hence of the change in apparent interaction cross section of the analyte ion, depends on both the stereochemistry and electronic charge distribution of the analyte ions and buffer gas molecules. The utility of this effect has been demonstrated using inorganic compounds such as $N_2$, $CO_2$ and $SF_6$.

Polarisability is a measure of the amount by which the electron cloud associated with a molecule may be distorted by proximity of an electric field (i.e. or electric charge) e.g. due to the proximity of a charged reagent or analyte ion. Polarisability, σ, may be expressed by:

$$\sigma = \frac{\mu}{E} \quad (1)$$

wherein μ is the induced dipole moment and E is the electric field.

When a charged analyte ion is in proximity to a polarisable gas molecule a charge-induced dipole interaction occurs. The potential energy for this interaction, $V_{ci}$, is given by:

$$V_{ci} = \frac{q^2 \sigma}{2R^4} \quad (2)$$

wherein q is charge of the ion, σ is the polarisability of the molecule and R is the distance between the charged ion and the polarisable molecule.

In general, the polarisability of a molecule increases with its electron cloud volume. Thus, for example, larger atoms tend to be more polarisable as their electrons are more loosely bound. For molecules, the larger the molecule the more highly polarisable the molecule will generally be. However, the polarisability also depends on how tightly bound or associated with each bond within the molecule the electrons are.

According to various embodiments it is recognised that by introducing polarisable buffer gases to an ion mobility separation device it is possible to selectively change or enhance the separation characteristics of the ion mobility separation device. In this way, the ion mobility separation peak capacity and specificity may be increased. That is, by suitably selecting, or changing, the buffer gas composition the apparent interaction cross sections for at least some of the analyte ions may be changed. It is also possible to select a buffer gas to specifically enhance the interactions for (at least) a particular analyte ion, and to therefore allow greater specificity in identification of known target ions.

According to various embodiments it is recognised that further improvements in this respect may be achieved by optimising the type of compounds used as the buffer gas i.e. by selecting as a buffer gas compounds that have a desired combination of physical and chemical properties.

Various embodiments will now be described.

Figure 1:
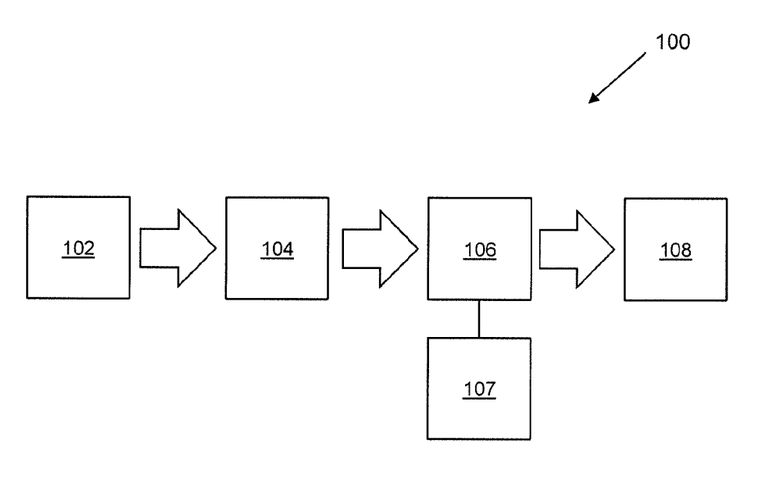
FIG. 1 shows schematically a mass spectrometer arrangement comprising an ion mobility or differential ion mobility separation device according to various embodiments.

FIG. 1 shows schematically a mass spectrometer arrangement 100 according to various embodiments. As is shown in FIG. 1, ions are passed from an ion source 102 to an upstream ion trap 104. Ions that are accumulated in the upstream ion trap 104 are then passed to an ion mobility or differential ion mobility separation device 106. Ions are then separated according to their ion mobility or differential ion mobility by virtue of their interactions with a buffer gas within the device 106. The device 106 also comprises a gas controller 107 that can adjust the composition of the buffer gas introduced to the device 106 so as to selectively change or enhance the separation characteristics of the device 106. The ions are then transferred to a TOF mass analyser 108 for mass analysis.

As will be appreciated, the arrangement shown in FIG. 1 is just one example of many possible arrangements comprising an ion mobility or differential ion mobility separation device to which the concepts described herein may equally be applied.

Embodiments which use volatile or gaseous polarisable aliphatic hydrocarbons as ion mobility separation buffer gas to enhance the ion-molecule interactions and provide large ion mobility separation peak capacities and selectivity are particularly advantageous. These hydrocarbons are particularly advantageous because, as will be seen below, hydrocarbons tend to be relatively highly polarisable (i.e. as a function of their molecular weight and/or size).

Another advantage associated with many aliphatic hydrocarbons is that they are volatile, and in many cases gaseous, at or close to room temperature (20° C.) and atmospheric pressure (1013 mbar). This is because hydrocarbons tend to have relatively low permanent dipole moments and hence the intermolecular forces between hydrocarbons tend to be relatively weak. In some cases e.g. where the hydrocarbon is symmetrical the permanent dipole moment may be zero. Where the permanent dipole moment is low, or zero, the main or only intermolecular forces may be relatively weak instantaneous dipole-induced dipole ("London dispersion") forces. The potential energy of this induced dipole-induced dipole interaction can be approximated by the London formula:

$$V_{AB} = -\frac{3}{2}\frac{\sigma_A \sigma_B}{r^6}\frac{I_A I_B}{I_A + I_B} \quad (3)$$

wherein $V_{AB}$ is the potential between molecules A and B due to this interaction, $I_{A/B}$ is the first ionization energy of molecule A/B, r is the distance between molecules A and B and $\sigma_{A/B}$ is the polarisability of molecules A/B.

Table 1 (below) shows a list of hydrocarbons that may be particularly suitable for use with the techniques of various embodiments. Table 1 lists the molecular weight, boiling point, polarisability and dipole moment of a number of hydrocarbons. These values (and those in Table 2, below) are taken from CRC Handbook of Chemistry and Physics, 87$^{th}$ edition (CRC Press).

It can be seen that all of the compounds listed in Table 1 have a relatively high polarisability. Furthermore, each of the hydrocarbons listed in Table 1 has a measured or calculated boiling point less than (or equal to) 30° C. at atmospheric pressure and is thus volatile or gaseous at room temperature (20° C.). This is despite in some cases the molecules containing many C—C and C—H bonds. As explained above this is because of their very low dipole moments which lead to relatively weak London dispersion forces acting between the hydrocarbon molecules.

It is advantageous for buffer gas compounds to be volatile or gaseous at room temperature (20° C.) because introducing different gaseous compounds into an ion mobility separation device is very simple compared to introducing liquid dopants, and allows a more quantitative control of the gas composition. This may thus facilitate selective adjustment or control of interactions between analyte ions and the buffer gas during an ion mobility separation.

As discussed above, larger molecules are generally more polarisable and may thus provide larger changes in apparent interaction cross sections when used as a buffer gas than smaller molecules. It can be seen from Table 1 that relatively large and highly polarisable hydrocarbons can be provided that are volatile or even gaseous at room temperature (20° C.). It can also be appreciated from Table 1 that these aliphatic hydrocarbon compounds exhibit relatively high polarisabilities for a given molecular weight.

For instance, and by contrast, $SF_6$ has a molecular weight of 146 and no permanent dipole (and hence is gaseous at room temperature (20° C.)) but its polarisability is only $6.54 \times 10^{-24}$ cm$^3$ compared to the hydrocarbon Butane which has a higher polarisability of $8.2 \times 10^{-24}$ cm$^3$ but a much lower molecular weight of only 58. This comparatively large polarisability is because the electrons in a C—C bond are more loosely bound than in an S—F bond. In addition, Butane is a linear extended molecule and therefore the electron cloud is more easily distorted by the presence of an external charge.

In other examples, 1-Pentene, Isopentane, 3-Methyl-1-butene, 1,4-Pentadiene, Neopentane, 3-Methyl-1-butyne, 1,1 Dimethylcyclopropane and 1,2,3,4-Tetraethynyl-1,3-cyclobutadiene each have five or more carbon atoms, and accordingly have relatively higher molecular weights and relatively higher polarisability, and yet are still volatile or gaseous at room temperature (20° C.) and atmospheric pressure (1013 mbar).

As a more specific example, 1,2,3,4-Tetraethynyl-1,3-cyclobutadiene has a molecular weight of 148 (similar to that of $SF_6$) but its polarisability is $18 \times 10^{-24}$ cm$^3$, about three times higher than that of $SF_6$. Furthermore, despite its high molecular weight (and its containing 12 carbon atoms), 1,2,3,4-Tetraethynyl-1,3-cyclobutadiene has a boiling point of −11 degrees Celsius and is therefore gaseous at room temperature (20° C.). This is largely due to the lack of permanent dipole moment exhibited by this structure due to its symmetry.

It is noted that even though for the purposes of this application it may be advantageous to use as a buffer gas compounds that are gases at or close to room temperature (20° C.), it is contemplated that other compounds e.g. hydrocarbon compounds with higher boiling points may also be used. For instance, it may be desirable to use hydrocarbons having very high molecular weights as these will generally have even higher polarisability, but these compounds will also tend to have higher boiling points. In this case the device and/or the interface through which the buffer gas is introduced into the device may be heated to allow these compounds to be introduced in a gaseous state.

The charge-induced dipole interaction, $V_{ci}$, is proportional to the reciprocal fourth power of the distance between the charged ion and the polarisable molecule. It will also be appreciated that another or a further way of increasing the strength of the charge induced-dipole interactions is to therefore allow the analyte ions and buffer gas molecules to be in close proximity to each other. It is therefore advantageous for the buffer gas molecules to have a low molecular radius. Again, aliphatic hydrocarbons like those listed in Table 1 are well-suited in this respect as they typically possess relatively high polarisability for a particular molecular weight and/or radius, and thus have characteristics that are ideal for optimising this type of interaction. That is, the series of aliphatic hydrocarbons described herein have comparatively high polarisability for relatively low molecular radii. For instance, the hydrocarbon Ethane has a polarisability of $4.5 \times 10^{-24}$ cm$^3$, a molecular weight of 30 and molecular radius of 2.2 Angstroms. By contrast, $CO_2$ has a lower polarisability of only $2.9 \times 10^{-24}$ cm$^3$ but a higher molecular weight (of 44) and a molecular radius of 2.46 Angstroms.

The ion-molecule interactions may further be enhanced due to charge-induced structural distortions or changes in conformation of the buffer gas molecules. This is effect is seen in many aliphatic hydrocarbons, for example many alkanes. Generally, the extent to which the presence of charge can distort the structure of the hydrocarbon molecule increases as the number of carbon atoms in the hydrocarbon increases, due to the larger number of degrees of freedom within the molecule. These structural distortions may accentuate the interaction between the analyte ions and the hydrocarbon buffer gas, and/or produce additional interactions based not only on polarisability but also on the stereochemistry of the buffer gas molecule and the analyte ion. These interactions thus allow for further enhancement of the separation characteristics of the ion mobility separation device.

Furthermore, a number of gaseous hydrocarbons, e.g. 1,1-Dimethylcyclopropane, are chiral. This may allow a further degree of selectivity in the ion/buffer gas interaction where some (or the targeted) analyte ions are chiral.

Although the alkenes and alkynes tend to be slightly less polarisable than alkanes (as their electrons are more tightly bound within the alkene/alkyne bond) it can be seen that they still offer very high polarisabilities compared to other non-hydrocarbon compounds and still remain volatile enough to be easily introduced as a gas.

A further advantage of using aliphatic hydrocarbons as an ion mobility separation buffer gas is that they are generally inert and non-corrosive and therefore will not result in damage to any internal structures within the ion mobility separation device.

It can thus be appreciated that the characteristics of aliphatic hydrocarbon compounds are particularly suited for use in an ion mobility separation buffer gas, as they provide a good balance of relatively low boiling points (or high volatility) and relatively high polarisabilities for their molecular weight or radius. These compounds therefore possess characteristics that are ideally suited for optimisation or enhancement of ion-molecule interactions (e.g. of the types discussed above) within the ion mobility separation device. By enhancing these interactions, the separation characteristics of the ion mobility separation device may be altered such that the peak capacity and/or specificity are increased. Depending on the nature of the analyte ions of interest, and the particular experiment being performed it will be understood that slightly different considerations may apply when selecting which compound to use as a buffer gas. For instance, where the analyte ion is known, it may be possible to pre-determine theoretically or via experiment the buffer gas compositions that provide best separation from adjacent species.

Although the series of aliphatic hydrocarbons discussed above are particularly suited for use as an ion mobility separation buffer gas, the skilled person will appreciate that the use of aliphatic hydrocarbons like those in Table 1 and the techniques described herein may be applied more generally in other embodiments. For instance, it is trivial to see that deuterated analogues of any or all suitable hydrocarbon compounds (e.g. those listed in Table 1) will have similar chemical properties and will be similarly suited for use with the techniques described herein, and indeed for the purposes of the various embodiments the term hydrocarbon is therefore also intended to include deuterated compounds where one or more hydrogen atoms is replaced by a deuterium atom.

Similarly, the skilled person will appreciate that compounds analogous to those discussed above (e.g. any or all of the compounds listed in Table 1) but having one or more carbon atoms replaced by silicon atoms will also have very similar chemical properties and thus also be suitable for use as an ion mobility separation buffer gas. The various embodiments therefore also extends to hydrosilicon or hydrosilane compounds such as those set out in Table 2 (below).

Table 2 lists a (non-exhaustive) selection of some hydrosilane compounds that are suitable for use with the techniques of the various embodiments. These compounds are not generally as commercially available but, advantageously, do tend to be slightly more polarisable than their hydrocarbon equivalents due to the larger size of the silicon atom.

Naturally, the recognition that compounds having a desired combination of relatively high polarisability and relatively low boiling points and/or molecular weights is not limited to aliphatic hydrocarbons and/or hydrosilanes and may also be extended to other suitable organic, organosilicon or silicon-based compounds. For instance, the skilled person will appreciate that aromatic compounds and/or more polar organic compounds may also be used as a buffer gas provided that they possess suitable properties, e.g. low boiling point, high polarisability, etc. or that the interface is heated or otherwise adapted to facilitate their introduction. It is also contemplated that halogenated compounds may be used, for example, fluorocarbon or hydrofluorocarbons compounds, to similar effect.

Any of the compounds described above may be introduced into an ion mobility separation device to provide for additional degrees of specificity. Thus the separation characteristics of the ion mobility separation device for a particular mixture of analyte ions may be altered by changing the composition of the buffer gas. This may allow enhancements in peak separation and/or in targeting specific analyte ions. The gas composition may comprise a controlled mixture of the compounds described above, the mixture being adjusted to enhance the separation characteristics for a particular sample of analyte ions. The gas composition may be changed from experiment to experiment, or may be changed in real-time during the course of an experiment, e.g. over the course of an liquid chromatography ("LC") or gas chromatography ("GC") injection.

Although the present invention has been described with reference to various embodiments, it will be understood by those skilled in the art that various changes in form and detail may be made without departing from the scope of the invention as set forth in the accompanying claims.

TABLE 1

| Structure | Name | Elemental composition | Molecular Weight | Boiling Point (Deg C.) | Polarisability ($10^{-24}$ cm$^3$) | Dipole moment (Debye) |
|---|---|---|---|---|---|---|
| $CH_4$ | Methane | $CH_4$ | 16.0425 | −164 | 2.6 | 0 |
|  | 1,3-Butadiene | $C_4H_6$ | 54.0904 | 4.5 | 8.64 | Trans = 0 Cis = 0.098 |

TABLE 1-continued

| Structure | Name | Elemental composition | Molecular Weight | Boiling Point (Deg. C.) | Polarisability ($10^{-24}$ cm$^3$) | Dipole moment (Debye) |
|---|---|---|---|---|---|---|
| H$_2$C=CH$_2$ | Ethylene | C$_2$H$_4$ | 28.0532 | −104 | 4.25 | 0 |
| H$_2$C=C(CH$_3$)CH$_3$ | 2-Methyl-1-Propene | C$_4$H$_8$ | 56.1063 | −7 | 8 | 0.5 |
| H$_3$C—CH$_2$—CH$_2$—CH$_3$ | Butane | C$_4$H$_{10}$ | 58.1222 | −0.6 | 8.2 | 0 |
| H$_2$C=CH—CH$_2$—CH$_3$ | 1-Pentene | C$_5$H$_{10}$ | 70.1329 | −1.7 | 9.65 | 0.624 |
| H$_3$C—CH$_3$ | Ethane | C$_2$H$_6$ | 30.069 | −88 | 4.5 | 0 |
| H$_3$C—CH$_2$—CH$_3$ | Propane | C$_3$H$_8$ | 44.0956 | −42 | 6.3 | 0.083 |
| (CH$_3$)$_2$CHCH$_2$CH$_3$ | Isopentane | C$_5$H$_{12}$ | 72.1488 | 28 | 10 | 0.105 |
| H$_3$C—CH=CH$_2$ (with CH$_3$) | 1-Butene | C$_4$H$_8$ | 56.1063 | −6.3 | 8 | 0.34 |
| (CH$_3$)$_2$CHCH$_3$ | Isobutane | C$_4$H$_{10}$ | 58.1222 | −11.7 | 8.1 | 0.13 |
| H$_3$C—C≡CH | 1-Propyne | C$_3$H$_4$ | 40.0639 | −23 | 6.18 | 0.8 |
| H$_2$C=C=CH$_2$ | Allene | C$_3$H$_4$ | 40.0639 | −34 | 6.1 | 0 |
| H$_2$C=CH—CH$_3$ | 1-Propene | C$_3$H$_6$ | 42.0797 | −48 | 6.2 | 0.366 |
| HC≡CH | Acetylene | C$_2$H$_2$ | 26.0373 | −84 | 3.3 | 0 |
| △ | Cyclopropane | C$_3$H$_6$ | 42.0797 | −33 | 5.7 | 0 |
| H$_3$C—C≡C—CH$_3$ | 2-Butyne | C$_4$H$_6$ | 54.0904 | 25 | 7.4 | 0 |
| H$_3$C—CH=CH—CH$_3$ | (2E)-2 Butene | C$_4$H$_8$ | 56.1063 | 1 | 8 | 0 |
| (CH$_3$)$_2$CH—CH=CH$_2$ | 3-Methyl-1-butene | C$_5$H$_{10}$ | 70.1329 | 20 | 9.9 | Trans = 0.32 Cis = 0.3898 |
| H$_2$C=CH—CH$_2$—CH=CH$_2$ | 1,4-Pentadiene | C$_5$H$_8$ | 68.117 | 26 | 9.8 | 0 |
| C(CH$_3$)$_4$ | Neopentane | C$_5$H$_{12}$ | 72.1488 | 9.5 | 10 | 0 |
| (CH$_3$)$_2$CH—C≡CH | 3-Methyl-1-butyne | C$_5$H$_8$ | 68.117 | 30 | 9.1 | 0.721 |

TABLE 1-continued

| Structure | Name | Elemental composition | Molecular Weight | Boiling Point (Deg C.) | Polarisability ($10^{-24}$ cm$^3$) | Dipole moment (Debye) |
|---|---|---|---|---|---|---|
| H$_3$C–CH=CH–CH$_3$ (cis) | (2Z)-2-Butene | C$_4$H$_8$ | 56.10632 | 3.7 | 8.2 | 0.25 |
| HC≡C—C≡CH | 1,3-Butadiyne | C$_4$H$_2$ | 50.0587 | 10 | 6.4 | 0 |
| HC≡C–CH$_2$–CH$_3$ | 1-Butyne | C$_4$H$_6$ | 54.0904 | 8 | 7.3 | 0.78 |
| (square) | Cyclobutane | C$_4$H$_8$ | 56.1063 | 12.5 | 7.3 | 0 |
| 1-Methylcyclopropene structure | 1-Methylcyclopropene | C$_4$H$_6$ | 54.0904 | 7 | 7.2 | 0.84 |
| H$_2$C=CH–C≡CH | 1-Buten-3-yne | C$_4$H$_4$ | 52.075 | 5.1 | 7.2 | 0.45 |
| Methylenecyclopropane structure | Methylene cyclopropane | C$_4$H$_6$ | 56.1063 | 8 | 7.2 | 0.4 |
| H$_2$C=C=CH–CH$_3$ | 1,2 Butadiene | C$_4$H$_6$ | 56.1063 | 11 | 8 | 0.403 |
| Cyclobutene structure | Cyclobutene | C$_4$H$_6$ | 56.1063 | 2 | 7.2 | 0.13 |
| Cyclopropene structure | Cyclopropene | C$_3$H$_4$ | 40.0639 | −27 | 5.3 | 0.36 |
| Methylcyclopropane structure | Methyl cyclopropane | C$_4$H$_6$ | 56.1063 | 1 | 7.4 | 0.14 |
| 1,1-Dimethylcyclopropane structure | 1,1Dimethyl-cyclopropane | C$_5$H$_{10}$ | 70.1329 | 20 | 9.2 | 0.142 |
| 3-Methylenecyclopropene structure | 3-Methylene-cyclopropene | C$_4$H$_4$ | 52.0746 | 26 | 7.1 | 0.402 |
| 1,2,3,4-Tetraethynyl-1,3-cyclobutadiene structure | 1,2,3,4-Tetraethynyl-1,3-cyclobutadiene | C$_{12}$H$_4$ | 148.1602 | −11 | 18 | 0 |

TABLE 2

| Structure | Name | Elemental composition | Molecular Weight | Boiling Point (Deg C.) | Polarisability ($10^{-24}$ cm$^3$) | Dipole moment (Debye) |
|---|---|---|---|---|---|---|
| (H$_3$C)$_4$Si structure | Tetramethylsilane | C$_4$H$_{12}$Si | 88.224 Da | 26 | 11.6 | |
| (H$_3$C)$_3$SiH structure | Trimethylsilane | C$_3$H$_{10}$Si | 74.197 | 6.7 | | |
| (H$_3$C)$_2$SiH$_2$ structure | Dimethylsilane | C$_2$H$_8$Si | 60.170 | −20 | | |
| H$_3$Si-CH$_2$-SiH$_3$ | Methylenedisilane | CH$_8$Si$_2$ | 76.245 | 17.6 | | |
| 1,2-Dimethyldisilane structure | 1,2-Dimethyldisilane | C$_2$H$_{10}$Si$_2$ | 90.03 | | | |
| Isopropylsilane structure | Isopropylsilane | C$_3$H$_{10}$Si | 74.055 | 13.8 | | |
| Siletane structure | Siletane | C$_3$H$_8$Si | 72.181 | 29.8 | | |
| H$_3$Si-CH=CH$_2$ | Vinylsilane | C$_2$H$_6$Si | 58.154 | −15.2 | | |
| H$_3$Si-C≡CH | Ethynylsilane | C$_2$H$_4$Si | 56.139 | 17.6 | | |

The invention claimed is:

1. A method of separating ions comprising:
providing an ion mobility or differential ion mobility separation device; and
causing ions to separate according to their ion mobility or differential ion mobility by virtue of their interactions with a buffer gas within said device, wherein said buffer gas comprises one or more organic, organosilicon or silicon-based compounds containing five or more carbon or silicon atoms, said one or more organic, organosilicon or silicon-based compounds being volatile or gaseous at room temperature (20° C.) and atmospheric pressure (1013 mbar) or having a boiling point of less than about: (i) 35° C.; (ii) 30° C.; (iii) 25° C.; (iv) 20° C.; or (v) 15° C. at atmospheric pressure (1013 mbar).

2. A method as claimed in claim 1, wherein said one or more organic, organosilicon or silicon-based compounds comprise one or more hydrocarbon, hydrosilicon or hydrosilane compounds.

3. A method as claimed in claim 1, wherein said one or more organic, organosilicon or silicon-based compounds comprise substantially 100% by volume of the total buffer gas composition.

4. A method as claimed in claim 1, wherein said one or more organic, organosilicon or silicon-based compounds are aliphatic.

5. A method as claimed in claim 1, further comprising selecting or altering the composition of said buffer gas to enhance the separation characteristics of said ion mobility or differential ion mobility separation device by controlling or altering the interactions between at least some of said ions and said buffer gas.

6. A method as claimed in claim 1, comprising selecting or adjusting the buffer gas composition to enhance or change the separation characteristics of said ion mobility or differential ion mobility separation device for a known analyte ion.

7. A method as claimed in claim 1, further comprising operating said ion mobility or differential ion mobility device at sub-atmospheric pressure.

8. A method as claimed in claim 1, wherein said buffer gas comprises one or more chiral organic, organosilicon or silicon-based compounds.

9. A method as claimed in claim 1, wherein said ions comprise or are derived from: (i) peptides; (ii) lipids; (iii) metabolites; (iv) carbohydrates; (v) drugs; (vi) pesticides; (vii) a biological sample; or (viii) a pharmaceutical sample.

10. A method as claimed in claim 1, further comprising:
analysing the or at least a portion of the ions according to their mass or mass to charge ratio; and
generating combined ion mobility and mass spectral data.

11. An ion mobility or differential ion mobility separator device arranged and adapted to cause ions to separate according to their ion mobility or differential ion mobility by virtue of their interactions with a buffer gas, wherein said buffer gas, in use, comprises one or more organic, organosilicon or silicon-based compounds containing five or more carbon or silicon atoms, said one or more organic, organo-silicon or silicon-based compounds being volatile or gaseous at room temperature (20° C.) and atmospheric pressure (1013 mbar) or having a boiling point of less than about: (i) 35° C.; (ii) 30° C.; (iii) 25° C.; (iv) 20° C.; or (v) 15° C. at atmospheric pressure (1013 mbar).

12. An ion mobility or differential ion mobility separator device as claimed in claim 11, further comprising a gas controller arranged and adapted to adjust the composition of said buffer gas introduced into said separator device, in use, so as to selectively change or enhance the separation characteristics of said separator device.

13. A mass spectrometer comprising:
an ion mobility or differential ion mobility separator device as claimed in claim 11; and
a mass analyser.

* * * * *